(12) United States Patent
Rao et al.

(10) Patent No.: US 12,398,114 B2
(45) Date of Patent: Aug. 26, 2025

(54) PROCESS FOR THE PREPARATION OF ELIGLUSTAT AND ITS INTERMEDIATE

(71) Applicant: PIRAMAL PHARMA LIMITED, Mumbai (IN)

(72) Inventors: Venkataramana Rao Rao, Telegana (IN); Sharadsrikar Kotturi, Gujarat (IN); Abdul Basith, Telegana (IN); Ramesh Babu Bandi, Telegana (IN); Manoj Kumar Mandadi, Telegana (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 693 days.

(21) Appl. No.: 17/438,068

(22) PCT Filed: Mar. 19, 2020

(86) PCT No.: PCT/IB2020/052492
§ 371 (c)(1),
(2) Date: Sep. 10, 2021

(87) PCT Pub. No.: WO2020/194138
PCT Pub. Date: Oct. 1, 2020

(65) Prior Publication Data
US 2022/0185788 A1  Jun. 16, 2022

(30) Foreign Application Priority Data
Mar. 22, 2019 (IN) .............. 201921011181

(51) Int. Cl.
*C07D 319/18* (2006.01)
*C07F 1/08* (2006.01)
*C07F 3/06* (2006.01)
*C07F 15/04* (2006.01)

(52) U.S. Cl.
CPC .............. *C07D 319/18* (2013.01); *C07F 1/08* (2013.01); *C07F 3/06* (2013.01); *C07F 15/045* (2013.01)

(58) Field of Classification Search
CPC . C07D 319/18; C07F 1/08; C07F 3/06; C07F 15/045
See application file for complete search history.

(56) References Cited

U.S. PATENT DOCUMENTS 7,196,205 B2  3/2007  Siegel et al.

FOREIGN PATENT DOCUMENTS

| CN | 105646442 A | 6/2016 |
| WO | 2003/008399 A1 | 1/2003 |
| WO | 2005/085178 A1 | 9/2005 |
| WO | 2015/059679 A1 | 4/2015 |
| WO | 2017/168313 A1 | 10/2017 |
| WO | 2018/193090 A2 | 10/2018 |

OTHER PUBLICATIONS

ISR for International Application PCT/IB2020/052492 mailed Jun. 23, 2020.
Written Opinion for International Application PCT/IB2020/052492 mailed Jun. 23, 2020.
Yu. N. Belokon et al., "General method of diastereo- and enantioselective synthesis of β-hydroxy-α-amino acids by condensation of aldehydes and ketones with glycine", J. Am. Chem. Soc., (19850000), vol. 107, pp. 4252-4259, XP055745507 [A] 2-10, 1985.
CN 105646442 A dated Jun. 8, 2016 _ 7 English Translation.

*Primary Examiner* — Laura L Stockton
(74) *Attorney, Agent, or Firm* — LADAS & PARRY LLP

(57) ABSTRACT

The present invention relates to an improved process for the preparation of N-((1R,2R)-1-(2,3-dihydrobenzo[b][1,4]dioxin-6-yl)-1-hydroxy-3-(pyrrolidin-1-yl)propan-2-yl)octanamide (A), which is known as ELIGLUSTAT and its pharmaceutically acceptable salts, comprising the formation of novel intermediate metal complex (III), which on hydrolysis in presence of acid provides amine compound (IV) (as described herein), which is treated with pyrrolidine and subsequently reduced to convert into Eliglustat (A).

9 Claims, 4 Drawing Sheets

(Scheme-1)

(Scheme-2)

PROCESS FOR THE PREPARATION OF ELIGLUSTAT AND ITS INTERMEDIATE

CROSS-REFERENCE TO RELATED APPLICATIONS

This application is a national phase entry under 35 USC 371 of International Patent Application No.: PCT/IB2020/052492 filed on 19 Mar. 2020, which claims the benefit of Indian Application No. 201921011181 filed on 22 Mar. 2019.

FIELD OF THE INVENTION

The present invention relates to an improved process for the preparation of N-((1R,2R)-1-(2,3-dihydrobenzo[b][1,4]dioxin-6-yl)-1-hydroxy-3-(pyrrolidin-1-yl)propan-2-yl)octanamide (A), which is known as ELIGLUSTAT and its pharmaceutically acceptable salts. The present invention also relates to a novel metal chiral complex (III) as an intermediate used for the preparation of Eliglustat.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

ELIGLUSTAT is chemically known as N-((1R,2R)-1-(2,3-dihydrobenzo[b][1,4]dioxin-6-yl)-1-hydroxy-3-(pyrrolidin-1-yl)propan-2-yl)octanamide and it is structurally represented by the following formula (A). Eliglustat (A) is marketed in the form of its tartrate salt under the brand CERDELGA® as capsules with dosages of EQ 84MG BASE for oral administration.

(A)

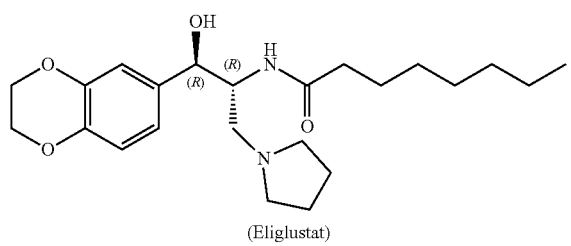

(Eliglustat)

CERDELGA® (Eliglustat) capsules, for oral use is approved in the USA as glucosylceramide synthase inhibitor indicated for the long-term treatment of adult patients with Gaucher disease type 1 who are CYP2D6 extensive metabolizers (EMs), intermediate metabolizers (IMs), or poor metabolizers (PMs) as detected by an FDA-cleared test.

Chirality has acquired increasing importance for the pharmaceutical industry, as evidenced by the fact that more than 80% of the drugs developed hitherto have chiral properties. The various enantiomers may develop completely different effects in the body, so that only one of two or more enantiomeric forms administered may be effective. In the case of Eliglustat (A), it has been observed that the (1R,2R) enantiomer is the desired isomer having desired activity. Administration of the active (1R,2R) enantiomer of the compound (A), substantially free of its other isomers, would essentially enable a reduction in the dose of drug. Due to the importance of the (1R,2R) enantiomer of the compound (A) as an oral, synthetic glucosylceramide synthase inhibitor, there exists a need to develop an economical and efficient synthetic process for its production.

U.S. Pat. No. 7,196,205 (hereinafter US'205) provides a process for the preparation of eliglustat (A) comprising formation of compound (5S)-5-Phenylmorpholin-2-One by the reaction of S-(+)-Phenyl glycinol with phenyl-α-bromo-acetate in the presence of diisopropylethylamine in acetonitrile solvent. The product further treated with benzodioxolane-6-carboxaldehyde under reflux condition provided cyclo adduct compound (1R,3S,5S,8aS)-1,3-Bis-(2',3'-dihydro-benzo[1,4]dioxin-6'-yl)-5-phenyl-tetrahydro-oxazolo[4,3-c][1,4]oxazin-8-one, which is treated with pyrrolidine to provide (2S,3R,1"S)-3-(2',3'-Dihydro-benzo[1,4]dioxin-6'-yl)-3-hydroxy-2-(2"-hydroxy-1"-phenyl-ethylamino)-1-pyrrolidin-1-yl-propan-1-one. The resultant keto compound undergoes reduction using lithium aluminum hydride to provide (1R,2R,1"S)-1-(2',3'-Dihydro-benzo[1,4]dioxin-6'-yl)-2-(2"-hydroxy-1"-phenyl-ethylamino)-3-pyrrolidin-1-yl-propan-1-ol. The compound was exposed to hydrogen pressure (110-120 psi) in the presence of trifluoroacetic acid and 20% Palladium hydroxide on carbon, to provide amine compound which on treatment with octanoic acid N-hydroxysuccinimide ester provides eliglustat (A). The procedure of patent US'205 is schematically represented in FIG. 2.

The PCT application WO 2017/168313A1 describes a process for preparation of optically active intermediate compound through the formation of the Nickel complex compound.

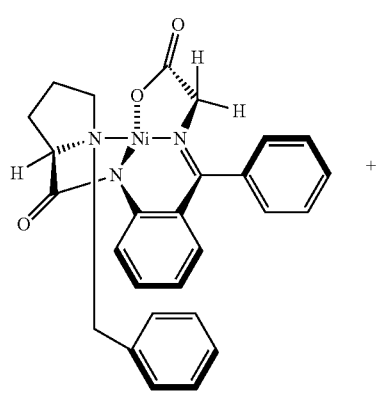

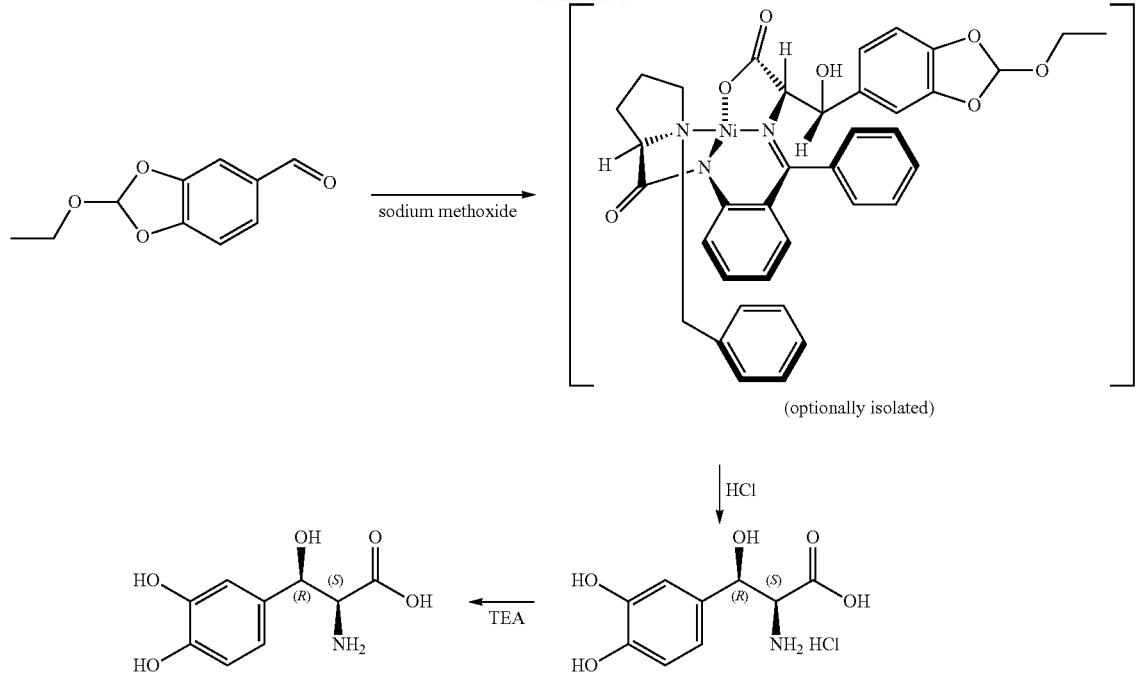
The PCT application WO 2018/193090 A2 disclosed a preparation process comprises steps such as oxidation, epimerization of the intermediate compounds during the formation of Eliglustat, as depicted below:
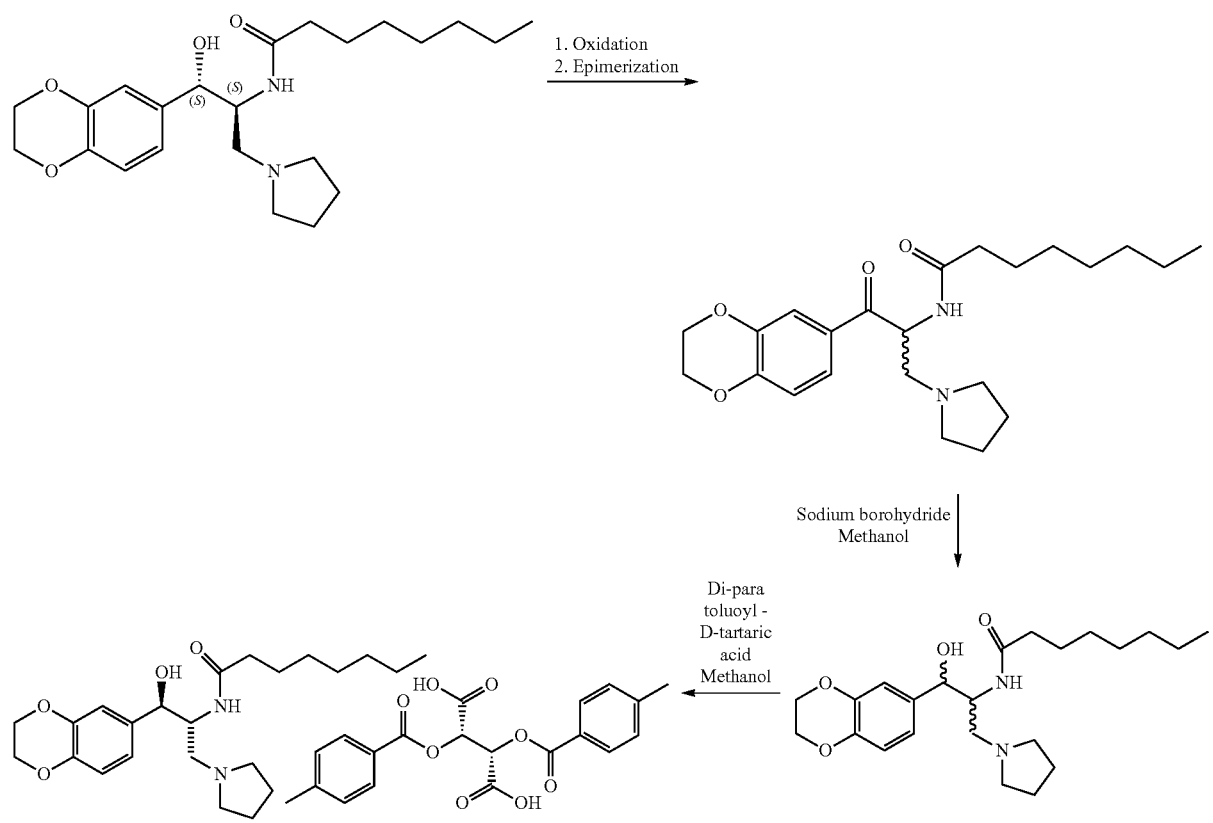

"Similarly, the *Am. Chem. Soc.* 107, 4252-59 (1985) disclosed hydrolysis of the metal complex to provide desired compound as shown in FIG. 1.

The PCT application WO 2005/085178 disclosed a method comprises the treatment of 1-hydroxy-1-(3, 4-dibenzyloxyphenyl) glycine-Ni-D-2-[N-(N'-benzylprolyl) amino]benzophenone with hydrochloric acid to obtain L-threo-(2S,3R)-3-(3,4-dibenzyloxyphenyl) serine. As indicated, the said compound has both the hydroxyl group protected with benzyl group forms 3,4-dibenzyloxyphenyl compound.

Several other methods for Eliglustat or its intermediate are known in the art such as Amino Acids, 45, 1017 (2003), PCT application WO 03/008399 and Chinese patent application CN105646442.

It is evident from the above discussion that the prior art processes for the preparation of Eliglustat involves multiple process steps such as resolution followed by separate deprotection method, use of chiral auxiliary, oxidation, and epimerization. The formation of cyclo-adduct, oxidations and epimerization renders the process costly. Also, the loss of product during the reported process is high and also requires recycling of the resolving agent by additional processing and is also associated with waste generation.

Therefore there is a need to develop an alternative asymmetric synthesis which would provide the desired (1R,2R) isomer of Eliglustat in an efficient and more specific manner. The said prior art processes are therefore disadvantageous for commercial manufacturing due to non-feasibility of the reaction process owing to use of toxic reagents, and due to the elaborate and tedious nature of the process, providing low yield of the desired isomer.

Inventors of the present invention have developed an improved process which is a simple, efficient and cost-effective process and provides the desired compounds in improved yield and purity and that addresses the problems associated with the processes reported in the prior art. The process of the present invention does not involve use of any toxic and/or costly solvents, also does not involve use of costlier coupling agents and reagents. Moreover, the process does not require repetitive purification steps. Accordingly, the present invention provides a process for the preparation of Eliglustat (A), which is simple, efficient, cost effective, environmentally friendly and commercially scalable for large scale operations.

SUMMARY OF THE INVENTION

Figure 1:
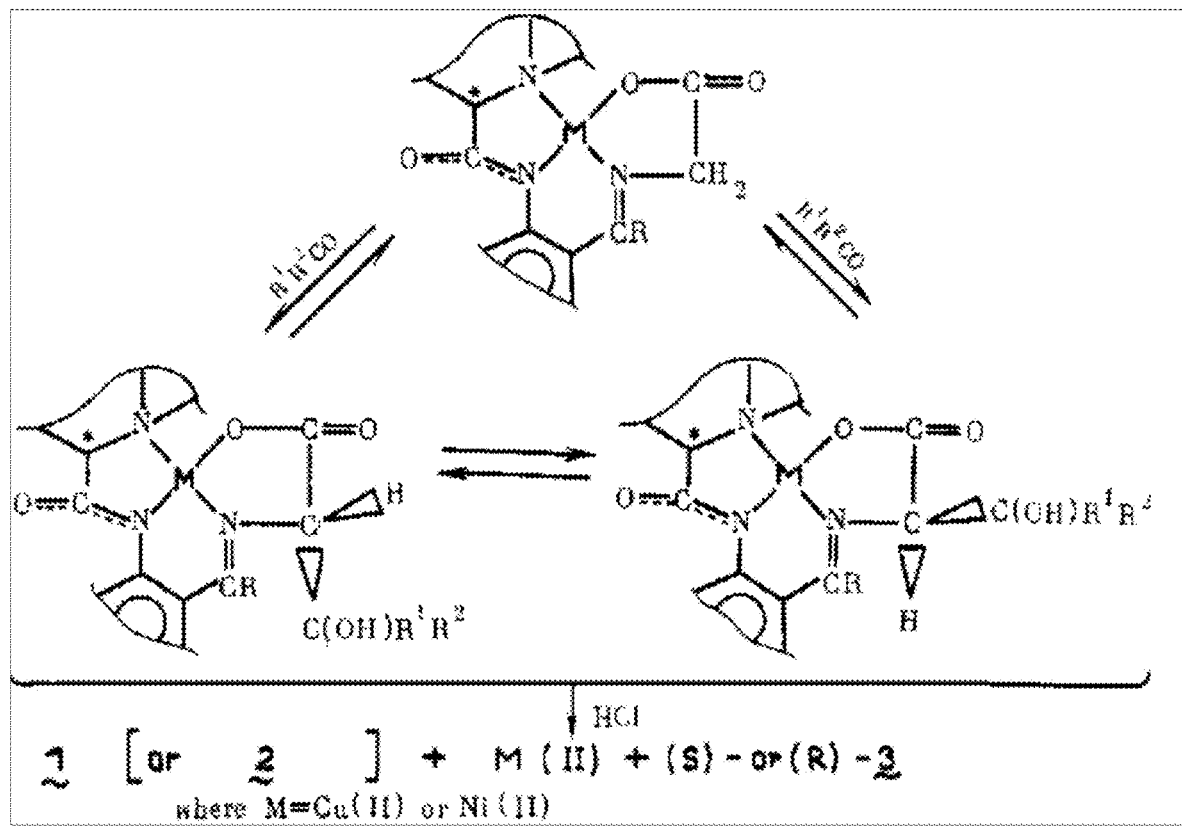
FIG. 1 shows a hydrolysis scheme from Am. Chem. Soc. 107, 4252-59 (1985).
Figure 2:
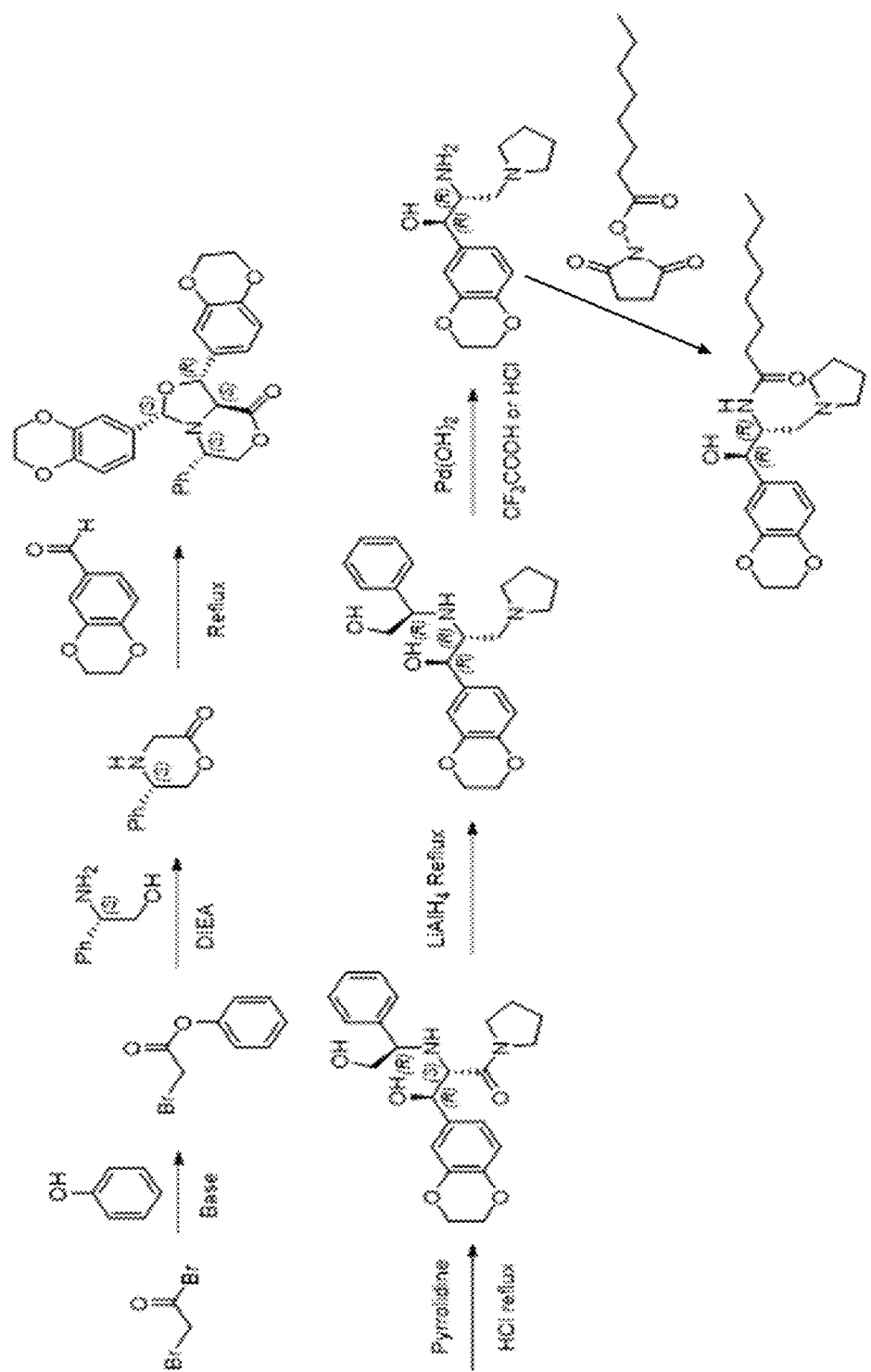
FIG. 2 shows a scheme from U.S. Pat. No. 7,196,205.

In one aspect, the present invention relates to an improved process for the preparation of N-((1R,2R)-1-(2,3-dihydrobenzo[b][1,4]dioxin-6-yl)-1-hydroxy-3-(pyrrolidin-1-yl) propan-2-yl)octanamide (A) [Eliglustat] or a salt thereof; comprising
(a) reaction of the aldehyde compound (II) (as described herein) with metal complex (I) (as described herein) in the presence of a base to obtain compound (III) (as described herein),
(b) hydrolysis of the compound (III) obtained from step (a) in presence of acid to obtain amine compound (IV) (as described herein),
(c) treating the amine compound (IV) of stage (b) with a protecting group to obtain amine protected compound (V) (as described herein),
(d) treating the amine protected compound (V) of stage (c) with pyrrolidine to obtain compound (VI) (as described herein),
(e) reducing the compound (VI) of stage (d) and converting to Eliglustat compound (A) or its salts.

In an embodiment, there is provided a novel intermediate metal complex (III);

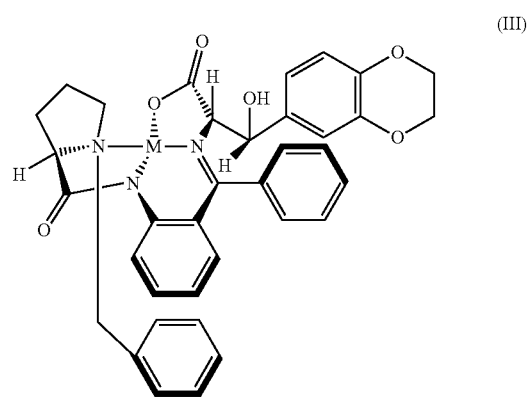

(III)

wherein M is a metal selected from $Cu^{2+}$, $Ni^{2+}$, or $Zn^{2+}$

In another aspect, there is provided a novel intermediate metal complex (IIIa);

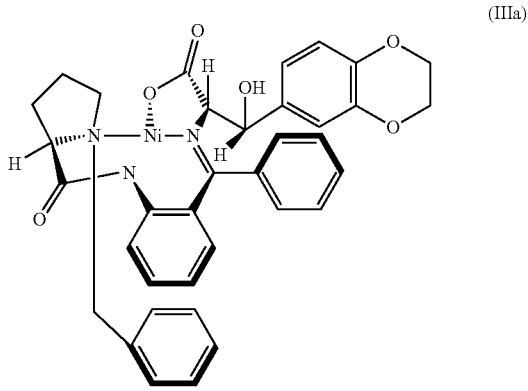

(IIIa)

In one aspect, the present invention relates to an improved process for the preparation of N-((1R,2R)-1-(2,3-dihydrobenzo[b][1,4]dioxin-6-yl)-1-hydroxy-3-(pyrrolidin-1-yl) propan-2-yl)octanamide (A) [Eliglustat] or a salt thereof; comprising
(i) reaction of the aldehyde compound (II) (as described herein) with nickel complex (Ia) (as described herein) in the presence of a alkoxide base to obtain compound (IIIa),
(ii) hydrolysis of the compound (IIIa) in presence of acid to obtain amine compound (IV),
(iii) treating the amine compound (IV) with a protecting group to obtain amine protected compound (V),
(iv) treating the amine protected compound (V) with pyrrolidine to obtain compound (VI), (v) reducing the compound (VI) in the presence of a reducing agent to obtain compound (VII), (vi) deprotecting the compound (VII) and treating with octanoic acid to obtain Eliglustat compound (A) or its salts.

In an embodiment, there is provided a novel trifluoroacetic acid (TFA) acid addition salt compound (VIIIa)

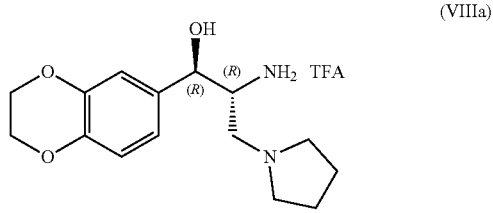
(VIIIa)

In an embodiment, there is provided N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] with more than 99% ee.

DETAILED DESCRIPTION OF THE INVENTION

Accordingly, the present invention relates to an improved process for the preparation of N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] or a salt thereof represented by the following formula,

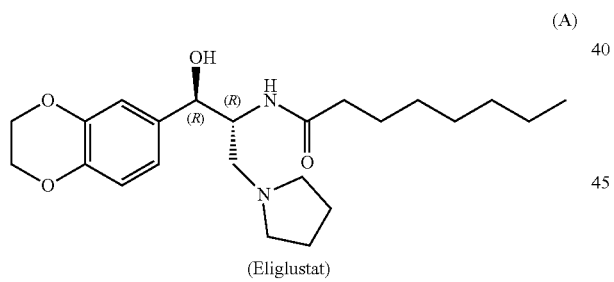
(A)
(Eliglustat)

comprising the steps of, (a) reacting the aldehyde compound (II) represented by the following formula,

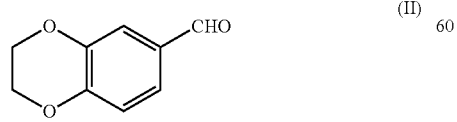
(II)

with metal complex compound (I) represented by the following formula,

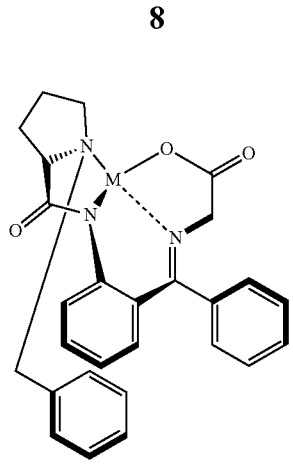
(I)

in the presence of a base to obtain compound (III):

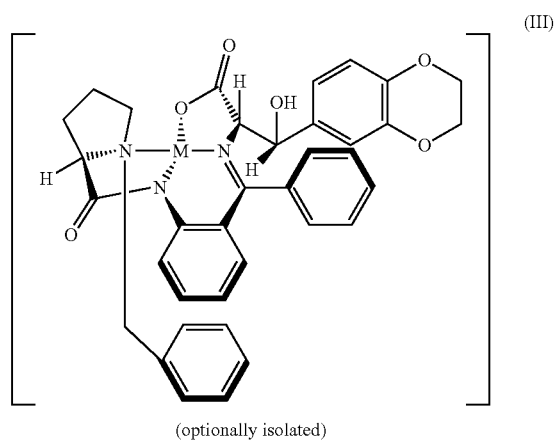
(III)
(optionally isolated)

wherein M is a metal selected from $Cu^{2+}$, $Ni^{2+}$, or $Zn^{2+}$ (b) hydrolysis of the compound (III) obtained from step (a) in presence of acid to obtain amine compound (IV) represented by the following formula,

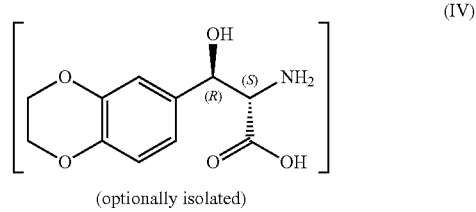
(IV)
(optionally isolated)

(c) treating the amine compound (IV) of stage (b) with a protecting group to obtain amine protected compound (V) represented by the following formula,

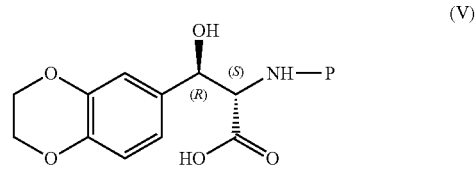
(V)

wherein P represents a protecting group.

(d) treating the amine protected compound (V) of stage (c) with pyrrolidine to obtain compound (VI) represented by the following formula,

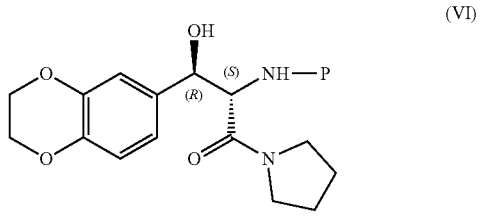

(e) reducing the compound (VI) of stage (d) and converting to Eliglustat compound (A) or its salts.

In the context of the present invention, the term 'hydrolysis' used in reference to any step of the reaction corresponds to the decomposition of metal complex (III).

Accordingly, in the process of the present invention the intermediate metal complex compound (III) is optionally isolated during reaction, or in-situ converted to the compound (IV) and subsequently to compound (V).

In an embodiment the 'base' is selected from the group consisting of inorganic base such as alkali hydroxide, alkali hydride, alkali carbonate, metal alkoxide; organic base such as alkyl amine, aryl amine, tertiary amine, or mixture thereof.

In an embodiment the 'metal alkoxide' is selected from the group consisting of sodium methoxide, sodium ethoxide, sodium isopropoxide, potassium methoxide, sodium tertiary butoxide, potassium tertiary butoxide, or mixtures thereof.

In an embodiment the 'acid' is selected from the group consisting of hydrochloric acid (HCl), hydrobromic acid, hydrofluoric acid, nitric acid, sulfuric acid and phosphoric acid or mixtures thereof.

In accordance with the embodiments of the present invention, the 'protecting group' is an amine protecting group which refers to the group tert-Butyloxycarbonyl (Boc), Fluorenylmethyloxycarbonyl (Fmoc), benzyloxycarbonyl (Cbz) and the like.

Accordingly, the present invention relates to an improved process for the preparation of N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] or a salt thereof represented by the following formula,

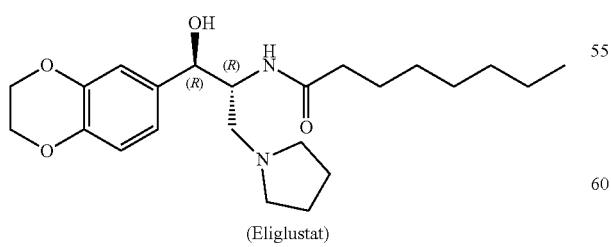

(Eliglustat)

comprising the steps of, (i) reacting the aldehyde compound (II) represented by the following formula,

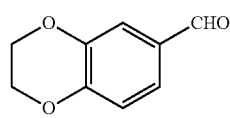

with nickel complex compound (Ia) represented by the following formula,

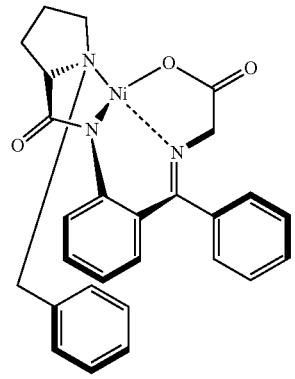

in the presence of a base to obtain compound (IIIa):

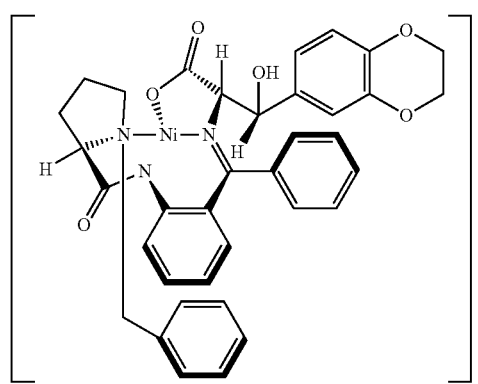

(optionally isolated)

(ii) hydrolysis of the compound (IIIa) obtained from step (i) in presence of acid to obtain amine compound (IV) represented by the following formula,

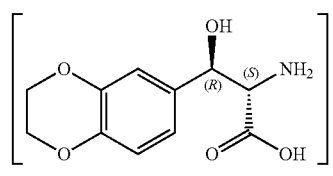

(optionally isolated)

(iii) treating the amine compound (IV) of stage (ii) with a protecting group to obtain amine protected compound (V) represented by the following formula,

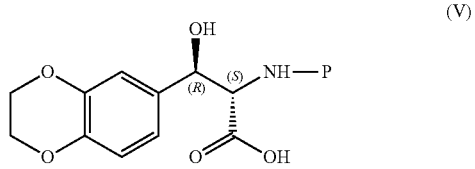

wherein P represents a protecting group.
(iv) treating the amine protected compound (V) of stage (iii) with pyrrolidine to obtain compound (VI) represented by the following formula,

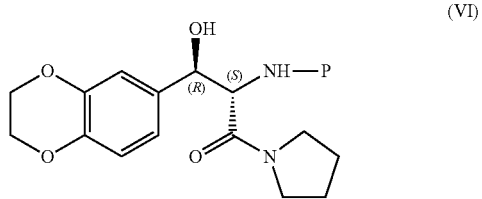

(v) reducing the compound (VI) of stage (iv) in the presence of a reducing agent to obtain compound (VII) represented by the following formula,

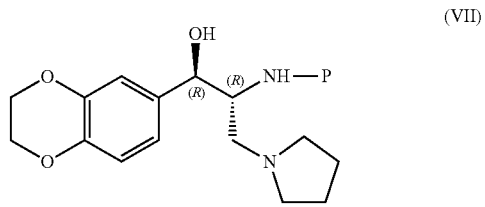

(vi) deprotecting the compound (VII) of stage (v) and treating with octanoic acid to obtain Eliglustat compound (A) or its salts.

In an embodiment the 'reducing agent' is selected from the group consisting of diborane, borane-dimethyl sulphide (DMS), borane-tetrahydrofuran (THF) complex, sodium triacetoxyborohydride, sodium cyanoborohydride, $NaBH_4$, $BF_3$·etherate, $LiBH_4$, diethyl methoxy borane+$NaBH_4$, Trialkyl boranes and the like.

In a specific embodiment, the process for the preparation of N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] or a salt thereof comprises the steps of,
(1) adding the compound (Ia) in a solvent,
(2) adding metal alkoxide and the aldehyde compound (II) to the reaction mixture of step (1),
(3) optionally isolating the compound (IIIa) obtained from step (2),
(4) adding an acid to the stirring solution containing compound (IIIa),
(5) optionally isolating the compound (IV) obtained from step (4),
(6) adding an amine protecting agent to the solution containing the compound (IV), (7) dissolving the compound (V) obtained from step (6) in solvent followed by the addition of pyrrolidine and a coupling agent to form compound (VI),
(8) dissolving the compound (VI) obtained from step (7) in solvent followed by the addition of reducing agent,
(9) treating the compound (VII) obtained from step (8) with an acid to form acid addition salt as compound (VIII), (10) treating the compound (VIII) with octanoic acid and isolating the desired product.

Figure 3:
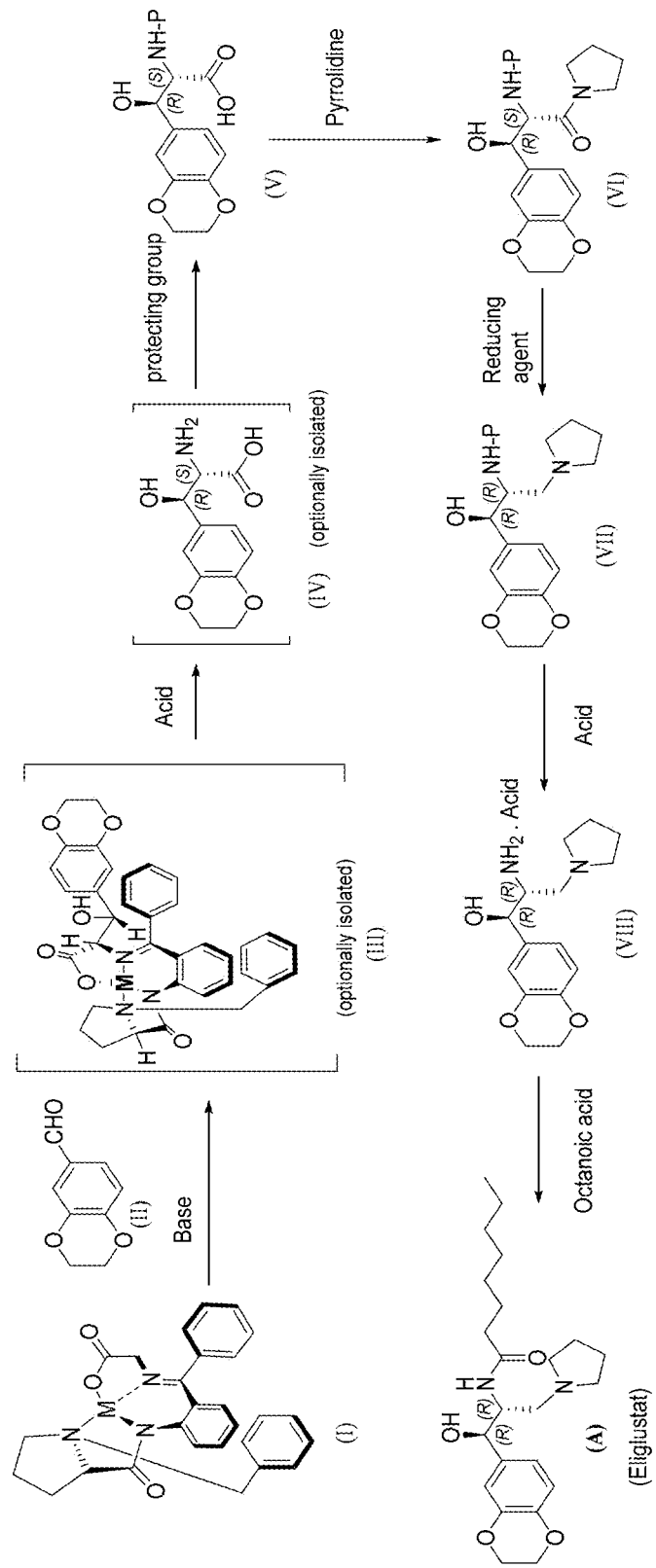
FIG. 3 shows Scheme (1).

The process of the present invention as per the specific embodiment described above is Scheme (1), shown in FIG. 3, wherein 'M' is a metal selected from $Cu^{2+}$, $Ni^{2+}$, or $Zn^{2+}$ and 'P' represents a protecting group The solvent used in the step (1) to step (10) of the above process (as depicted in the Scheme-1) is selected from a halogenated solvent such as dichloromethane, 4-bromotoluene, diiodomethane, carbon tetrachloride, chlorobenzene, ethylene chloride and chloroform; alcoholic solvent such as methanol, ethanol, isopropanol, t-amyl alcohol, t-butyl alcohol and hexanol; an ether solvent such as tetrahydrofuran (THF), cyclopentyl methyl ether, methyl tert-Butyl ether (MTBE), 2-methyltetrahydrofuran, diethyl ether and 1,4-dioxane; a ketone selected from methyl ethyl ketone, acetone, methyl isobutyl ketone (MIBK), ethyl methyl ketone; an ester selected from ethyl acetate, isopropyl acetate; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; acetone; water or a mixture thereof.

The metal alkoxide used in the step (2) of the above process (as depicted in the Scheme (1)) is selected from the sodium methoxide, sodium ethoxide, sodium isopropoxide, potassium methoxide, sodium tertiary butoxide, potassium tertiary butoxide, or a mixture thereof.

The term 'isolating' referred to in the step (3), step (5) and step (10) of the above process (as depicted in the Scheme (1)) corresponds to the steps involving biphasic separation, separation of organic phase, filtration, evaporation of solvent, cooling, precipitation, washing and/or drying.

The acid used in the step (4) of the above process (as depicted in the Scheme (I)) is selected from hydrochloric acid, hydrobromic acid, hydrofluoric acid, nitric acid, sulfuric acid and phosphoric acid or a mixture thereof.

The protecting agent used in the step (6) of the above process (as depicted in the Scheme (1)) which corresponds to the group tert-Butyloxycarbonyl (Boc), Fluorenylmethyloxycarbonyl (Fmoc), benzyloxycarbonyl (Cbz) and the like.

The coupling agent used in the step (7) of the above process (as depicted in the Scheme (1)) is selected from O-(Benzotriazol-1-yl)-N N N'N'-tetramethyluronium tetrafluoroborate (TBTU), N,N'-Dicyclohexylcarbodiimide (DCC), (2-(1H-benzotriazol-1-yl)-1,1,3,3-tetramethyluronium hexafluorophosphate (HBTU), 1-[Bis(dimethylamino)methylene]-1H-1,2,3-triazolo[4,5-b]pyridinium 3-oxid hexafluorophosphate (HATU), 3-(diethoxyphosphoryloxy)-1,2,3-benzotriazin-4(3H)-one (DEPBT), benzotriazol-1-yl-oxytripyrrolidinophosphonium hexafluorophosphate (PyBOP).

The 'acid addition salt' formed in the step (9) of the above process (as depicted in the Scheme (1)) refers to the acid selected from trifluoroacetic acid (TFA), hydrochloric acid, hydrobromic acid, hydrofluoric acid, nitric acid, sulfuric acid and phosphoric acid or a mixture thereof.

Figure 4:
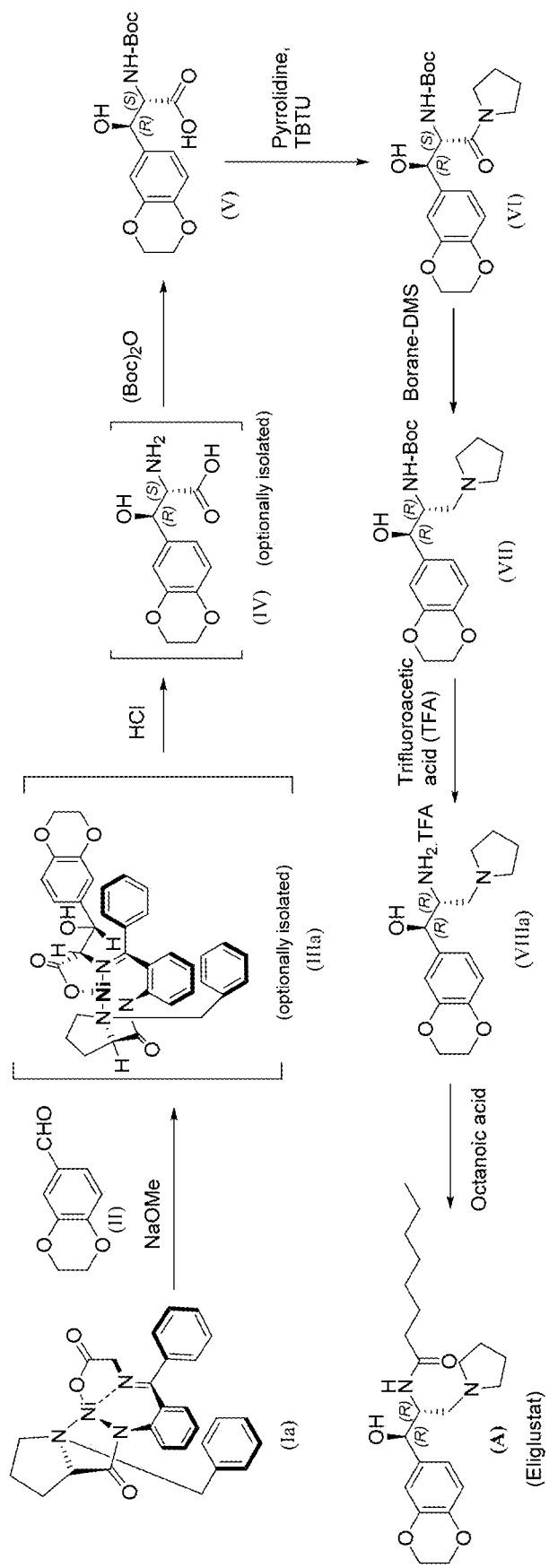
FIG. 4 shows Scheme (2).

The overall process of the present invention involving preparation of N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] or a salt thereof via formation of intermediate compound (IIIa) is Scheme (2) shown in FIG. 4.

The process illustrated in the above scheme (2) comprises reaction of the compound (Ia) with 2,3-dihydrobenzo[b][1,4]dioxine-6-carbaldehyde (II) in the presence of a metal alkoxide selected from sodium methoxide to obtain compound (IIIa) which is optionally isolated or in-situ hydrolysed by the treatment with an acid selected from hydrochloric acid to obtain the compound (IV), which is optionally isolated and was treated with di-tert-butyl dicarbonate reagent to form N-Boc compound (V). Further, the (2S,3R)-2-((tert-butoxycarbonyl)amino)-3-(2,3-dihydrobenzo[b][1,4]dioxin-6-yl)-3-hydroxypropanoic acid compound (V) was dissolved in THF and treated with pyrrolidine in the presence of TBTU to form compound (VI). The compound tert-butyl((1R,2S)-1-(2,3-dihydrobenzo[b][1,4]dioxin-6-yl)-1-hydroxy-3-oxo-3-(pyrrolidin-1-yl)propan-2-yl)carbamate compound (VII) was further reduced using Borane-dimethyl sulfide complex. The obtained compound was treated with trifluoroacetic acid to provide TFA acid addition salt as compound (VIIIa). Finally, the compound was treated with octanoic acid to provide Eliglustat (A) with more than 99% ee.

The inventors of the process of the instant invention observed that the elemental impurity content of the final product Eliglustat (A) obtained by this process is very low and does not require any specific purification technology to remove elemental impurities such Nickel (Ni).

Accordingly, it is also evident that the product Eliglustat (A) obtained by the process of the instant invention has a high enantiomeric excess (ee).

In an another embodiment, there is provided N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] with more than 99% ee.

In an another embodiment, there is provided N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] with more than 99.5% ee.

In an another embodiment, there is provided N-((1R,2R)-1-(2,3-dihydrobenzo[b][1,4]dioxin-6-yl)-1-hydroxy-3-(pyrrolidin-1-yl)propan-2-yl)octanamide (A) [Eliglustat] with more than 99.99% ee.

In an embodiment, there is provided a novel intermediate metal complex (III);

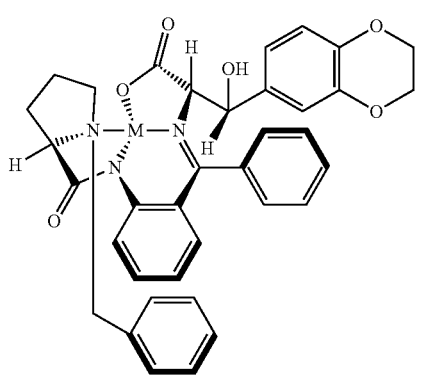

(III)

wherein M is a metal selected from $Cu^{2+}$, $Ni^{2+}$, or $Zn^{2+}$

In an embodiment, there is provided a novel intermediate metal complex (IIIa);

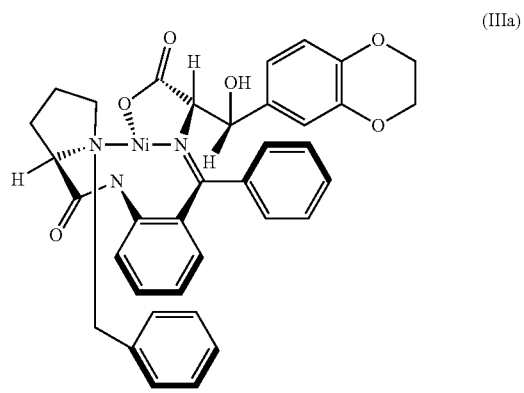

(IIIa)

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1: Preparation of (2S,3R)-2-((tert-butoxycarbonyl)amino)-3-(2,3-dihydrobenzo[b][1,4]dioxin-6-yl)-3-hydroxypropanoic acid (V)

Charged 125 mL of methanol in a flask followed by the addition of sodium methoxide (250 mmol) at temperature of about 25-30° C. and cooled to 0-10° C. temperature. To the reaction mixture was added 25 g of Nickel complex (Ia) and (25 g, 50 mmol) 2,3-dihydrobenzo[b][1,4]dioxine-6-carbaldehyde compound (II). The reaction mixture was stirred for about 1 h and quenched using 25 mL of concentrated hydrochloric acid. The reaction mixture was evaporated under vaccuo and crude mixture was diluted with 2N hydrochloric acid (38 mL). The precipitated solid was filtered. The aqueous layer was extracted with dichloromethane (100 mL) and washed with ethyl acetate (2×100 mL). The filtrate was taken in a flask followed by the addition of ammonium pyrrolidine dithiocarbamate (PDTC, 14.0 g), and the solution was heated to 70-75° C. for about 1 h. The obtained solids were filtered, washed with isopropyl alcohol (50 mL), and the aqueous layer was evaporated to obtain (2S,3R)-2-amino-3-(2,3-dihydrobenzo[b][1,4]dioxin-6-yl)-3-hydroxypropanoic acid (IV).

The crude material was diluted with 1,4 dioxane (100 mL) and water (50 mL) at a temperature of 25-30° C. To the reaction mixture was added triethylamine (24 mL) and added ditert-butyl dicarbonate (19.0 g), and the reaction mixture was stirred for about 16 h. The reaction mixture was evaporated under vacuum and the crude was diluted with ethyl acetate (70 mL). The mixture was acidified with citric acid (10%) and the organic layer was separated. The aqueous layer was extracted with ethyl acetate (2×35 mL) and the combined organic layer was evaporated under vacuum to provide the compound (V) (yield: 9.2 g, (54% from two stages); HPLC purity: 94.38%).

Example-2: Preparation of tert-butyl ((1R,2S)-1-(2,3-dihydrobenzo[b][1,4]dioxin-6-yl)-1-hydroxy-3-oxo-3-(pyrrolidin-1-yl)propan-2-yl)carbamate (VI)

Charged 112 mL of tetrahydrofuran in a flask followed by the addition of (2S,3R)-2-((tert-butoxycarbonyl)amino)-3-

(2,3-dihydrobenzo[b][1,4]dioxin-6-yl)-3-hydroxy-propanoic acid (V), pyrrolidine (1.87 g, 262 mmol), diisopropyl ethylamine (DIPEA) (8.4 g, 651 mmol) and TBTU (7.72 g, 240 mmol) at a temperature of 25-30° C. The reaction mixture was evaporated under vacuum and the crude was diluted with ethyl acetate (160 mL). The separated organic layer was washed with 10% citric acid solution (2×40 mL) and 5% sodium bicarbonate (2×40 mL). The organic layer was evaporated to provide compound (VI) (yield: 4.5 g, 52%).

Example-3: Preparation of tert-butyl ((1R,2R)-1-(2,3-dihydrobenzo[b][1,4]dioxin-6-yl)-1-hydroxy-3-(pyrrolidin-1-yl)propan-2-yl)carbamate (VII)

Charged 27 mL of tetrahydrofuran in a flask followed by the addition of tert-butyl ((1R,2S)-1-(2,3-dihydrobenzo[b][1,4]dioxin-6-yl)-1-hydroxy-3-oxo-3-(pyrrolidin-1-yl)propan-2-yl) carbamate (VI) (1.5 g, 38 mmol) and Borane-dimethyl sulfide complex (8.1 mL, 106 mmol) at a temperature of about 0-5° C. The reaction mixture was further stirred for about 2 h at a temperature of about 45-50° C. The recation mixture was quenched by the addition of methanol (82 mL) and the reaction mixture was evaporated under vacuum. The crude reaction mixture was diluted with ethyl acetate (82 mL) and washed with water (40 mL). The organic layer was evaporated to provide compound (VII) (yield: 0.9 g, 62.5%)

Example-4: Preparation of (1R,2R)-2-amino-1-(2,3-dihydrobenzo[b][1,4]dioxin-6-yl)-3-(pyrrolidin-1-yl)propan-1-ol (VIIIa) And Conversion into Eliglustat (A)

Charged 12 mL of dichloromethane in a flask followed by the addition of tert-butyl ((1R,2R)-1-(2,3-dihydrobenzo[b][1,4]dioxin-6-yl)-1-hydroxy-3-(pyrrolidin-1-yl)propan-2-yl)carbamate (VII) and trifluoroacetic acid (3 mL) at a temperature of about 10-15° C. The reaction mixture was stirred for 4 h at temperature of about 25-30° C. and evaporated under vacuum to provide (1R,2R)-2-amino-1-(2,3-dihydrobenzo[b][1,4]dioxin-6-yl)-3-(pyrrolidin-1-yl)propan-1-ol (VIIIa).

The compound (VIIIa) was dissolved in tetrahydrofuran (15 mL) followed by the addition of n-octanoic acid (0.13 g, 9 mmol), diisopropylethylamine (DIPEA) (2.0 mL, 15 mmol) and TBTU (1.22 g, 25 mmol). The reaction mixture was stirred for 16 h and the evaporated under vacuum. The crude was diluted with ethyl acetate (40 mL) and washed with 5% citric acid (2×20 mL), 5% sodium bicarbonate (2×20 mL). The organic layer was evaporated and crude compound was purified by preparative HPLC to provide Eliglustat (A).

We claim:

1. A process for preparing N-((1R,2R)-1-(2,3-dihydrobenzo[b][1,4]dioxin-6-yl)-1-hydroxy-3-(pyrrolidin-1-yl)propan-2-yl)octanamide (A) (Eliglustat) or a salt thereof, having a purity greater than 99.5% ee, represented by the following formula,

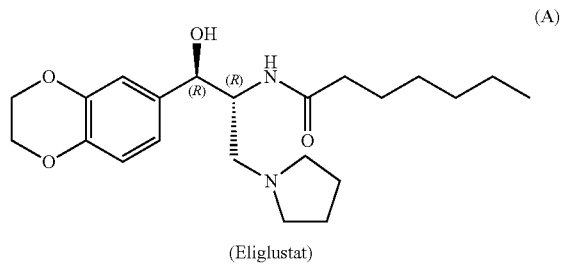

(Eliglustat)

comprising the steps of:

(i) reacting the aldehyde compound (II) represented by the following formula,

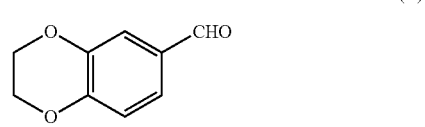

with nickel complex compound (Ia) represented by the following formula,

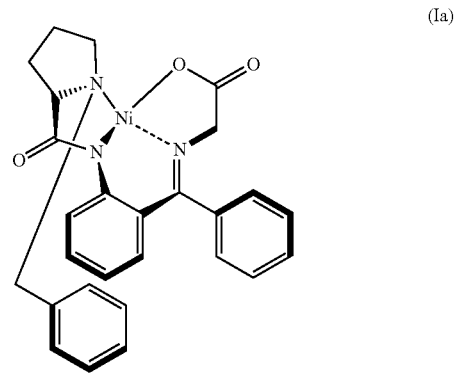

in the presence of a base to obtain compound (IIIa):

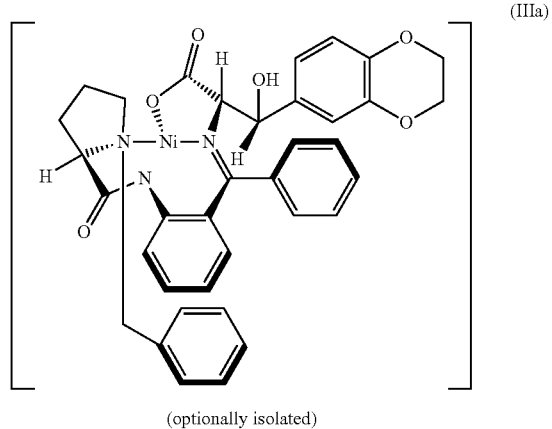

(optionally isolated)

(ii) hydrolysis of the compound (IIIa) obtained from step (i) in presence of acid to obtain amine compound (IV) represented by the following formula,

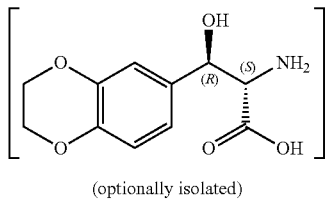

(IV)

(optionally isolated)

(iii) treating the amine compound (IV) of stage (ii) with a protecting group to obtain amine protected compound (V) represented by the following formula,

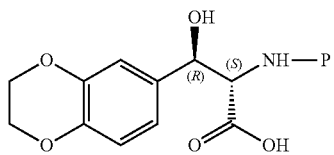

(V)

wherein P representing group, (iv) treating the amine protected compound (V) of stage (iii) with pyrrolidine to obtain compound (VI) represented by the following formula,

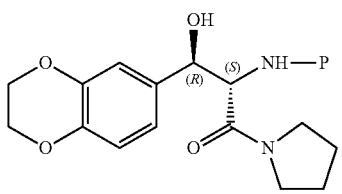

(VI)

(v) reducing the compound (VI) of stage (iv) in the presence of a reducing agent to obtain compound (VII) represented by the following formula,

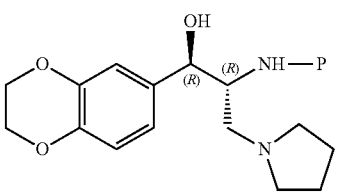

(VII)

(vi) deprotecting the compound (VII) of stage (v) and treating with octanoic acid to obtain Eliglustat compound (A) or a salt thereof, wherein Eliglustat (A) is obtained with a purity greater than 99.5% ee.

2. The process according to claim 1, further comprising:
(1) in step (i) adding the compound (Ia) in a solvent;
(2) adding metal alkoxide selected from sodium methoxide, sodium ethoxide, sodium isopropoxide, potassium methoxide, sodium tertiary butoxide, potassium tertiary butoxide, or a mixture thereof, and the aldehyde compound (II) to the reaction mixture of step (i);

(3) optionally isolating the compound (IIIa) obtained from step (i);
(4) adding an acid to the stirring solution containing compound (IIIa);
(5) optionally isolating the compound (IV) obtained from step (ii);
(6) adding an amine protecting agent to the solution containing the compound (IV);
(7) dissolving the compound (V) obtained from step (iii) in a solvent followed by the addition of pyrrolidine and a coupling agent to form compound (VI);
(8) dissolving the compound (VI) obtained from step (iv) in a solvent followed by the addition of a reducing agent;
(9) treating the compound (VII) obtained from step (v) with an acid to form acid addition salt as compound (VIII),

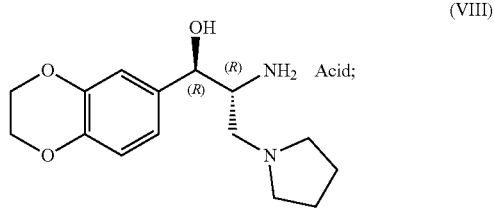

(VIII)

and

(10) treating the compound (VIII) with octanoic acid and isolating the desired product.

3. The process according to claim 2, wherein the acid used in the step (4) is selected from hydrochloric acid, hydrobromic acid, hydrofluoric acid, nitric acid, sulfuric acid and phosphoric acid or a mixture thereof.

4. The process according to claim 2, wherein the protecting agent used in the step (6) is selected from tert-Butyloxycarbonyl (Boc), Fluorenylmethyloxycarbonyl (Fmoc), or benzyloxycarbonyl (Cbz).

5. The process according to claim 2, wherein the coupling agent used in the step (7) is selected from O-(Benzotriazol-1-yl)-N,N,N'N'-tetramethyluronium tetrafluoroborate (TBTU), N,N'-Dicyclohexylcarbodiimide (DCC), (2-(1H-benzotriazol-1-yl)-1,1,3,3-tetramethyluronium hexafluorophosphate (HBTU), 1-[Bis(dimethylamino)methylene]-1H-1,2,3-triazolo[4,5-b]pyridinium 3-oxid hexafluorophosphate (HATU), 3-(diethoxyphosphoryloxy)-1,2,3-benzotriazin-4 (3H)-one (DEPBT), or benzotriazol-1-yl-oxytripyrrolidinophosphonium hexafluorophosphate (PyBOP).

6. The process according to claim 2, wherein the solvent used step (1) is an alcohol selected from methanol, ethanol, or isopropanol and the solvent used in step (7) and step (8) is an ether solvent selected from tetrahydrofuran (THF), cyclopentyl methyl ether, methyl tert-Butyl ether (MTBE), 2-methyltetrahydrofuran, diethyl ether, or 1,4-dioxane.

7. The process according to claim 2, wherein the reducing agent used in step (8) is selected from diborane, borane-dimethyl sulphide (DMS), borane-tetrahydrofuran (THF) complex, sodium triacetoxyborohydride, sodium cyanoborohydride, NaBH$_4$,BF$_3$·etherate, LiBH$_4$, diethyl methoxy borane+NaBH$_4$, or trialkyl boranes.

8. The process according to claim 2, wherein the acid in step (9) is selected from trifluoroacetic acid (TFA), hydrochloric acid, hydrobromic acid, hydrofluoric acid, nitric acid, sulfuric acid and phosphoric acid or a mixture thereof.

9. An intermediate metal complex (III);
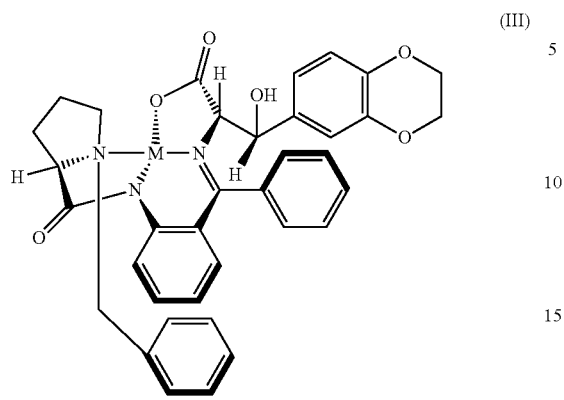
wherein M is a metal selected from $Cu^{2+}$, $Ni^{2+}$, or $Zn^{2+}$.
* * * * *